United States Patent [19]

Leaf et al.

[11] Patent Number: 5,541,225
[45] Date of Patent: Jul. 30, 1996

[54] α-LINOLENIC ACID AND EICOSATETRAYNOIC ACID IN THE PREVENTION AND TREATMENT OF VENTRICULAR TACHYARRHYTHMIA

[75] Inventors: Alexander Leaf, Winchester; Jing X. Kang, Quincy, both of Mass.

[73] Assignee: The General Hospital Corporation, Boston, Mass.

[21] Appl. No.: 320,873

[22] Filed: Oct. 11, 1994

[51] Int. Cl.⁶ .................................................. A61K 31/20
[52] U.S. Cl. ............................................................. 514/560
[58] Field of Search ............................................. 514/560

[56]  References Cited

PUBLICATIONS

Murnaghan "Effect of Fatty Acids on the Ventricular Arrhythmia Threshold in the Isolated Heast of the Rabbit" British Journal Pharmacology (1981) 73, 909–915.

*Primary Examiner*—Jeffrey Mullis
*Attorney, Agent, or Firm*—Fish & Richardson P.C.

[57] ABSTRACT

Methods and compositions for the prevention of imminent ventricular tachyarrhythmia, particularly ventricular fibrillation, are disclosed. The composition comprises α-linolenic acid, eicosatetraynoic acid (ETYA), or a mixture of α-linolenic acid and ETYA. The composition may be administered by intravenous infusion, intracardial injection or both in a patient who presents symptoms of a condition, such as myocardial ischemia associated with myocardial infarction, which may immediately lead to ventricular fibrillation.

22 Claims, No Drawings

α-LINOLENIC ACID AND EICOSATETRAYNOIC ACID IN THE PREVENTION AND TREATMENT OF VENTRICULAR TACHYARRHYTHMIA

STATEMENT AS TO FEDERALLY SPONSORED RESEARCH

This invention was made with government support under grant number RO1-DK38165 awarded by the National Institutes of Health. The government has certain rights to the invention.

BACKGROUND OF THE INVENTION

The invention relates to the prevention and/or termination of malignant ventricular tachyarrhythmia, particularly ventricular fibrillation. Ventricular tachyarrhythmia can be followed by ventricular fibrillation, which can lead to sudden death, and occurs primarily in patients having cardiomyopathies, such as myocardial ischemia, myocardial infarction, or other conditions which cause ischemia of cardiac tissue. The high incidence of recurrent ventricular fibrillation and sudden death in survivors of cardiac arrest underscores the need for an effective approach to prophylactic treatment in these patients.

SUMMARY OF THE INVENTION

In general, the invention features the intravenous administration of the omega 3 fatty acid α-linolenic acid and/or the arachidonic acid analog, eicosatetraynoic acid (ETYA), for the prevention of malignant ventricular tachyarrhythmia, particularly ventricular fibrillation, more particularly imminent ventricular fibrillation, in susceptible patients, or the termination of existing ventricular fibrillation in a patient. Patients who may be treated according to the subject invention include those who present with heart attack symptoms, are experiencing anaphylactic shock (e.g., induced by a bee sting), have a pre-existing condition such as a previous myocardial infarction, are receiving treatment by electrical stimulation or with antiarrhythmic drugs which may have adverse side effects, have a potentially lethal arrhythmia, or present with a condition which is associated with myocardial electrical instability, ion imbalance or non-ischemic cardiomyopathy.

Preferably, an intravenous infusion of a preparation of α-linolenic acid and/or ETYA is administered as an emergency treatment of a patient identified as being susceptible to ventricular tachyarrhythmia, particularly ventricular fibrillation. Patients who are susceptible to ventricular tachyarrhythmia, and thus likely susceptible to ventricular fibrillation, include patients who present with heart attack symptoms such as chest pain, light-headedness or dizziness, faintness, shortness of breath and electrocardiographic abnormalities. The infusion treatment may be continued until the patient is stabilized and appears to no longer be at risk of imminent ventricular fibrillation.

Alternatively, the patient requiring emergency treatment may receive treatment by direct injection of the α-linolenic acid and/or ETYA preparation into the heart or an artery of the heart. Administration of this initial bolus of α-linolenic acid and/or ETYA may be followed by continuous intravenous infusion.

In a further embodiment, intravenous infusion of the α-linolenic acid and/or ETYA preparation may be initiated prior to and/or during surgery where the patient is at risk of ventricular tachyarrhythmia, particularly ventricular fibrillation, due to a history of myocardial infarction or other heart condition. In particular, patients who are undergoing open heart surgery (e.g. coronary by-pass grafts) may be at particular risk of imminent ventricular fibrillation. Patients whose hearts have been arrested by cooling and high potassium are at particular risk of ventricular fibrillation during rewarming of the heart and attempts to initiate normal heart beats.

In a preferred embodiment, a patient presenting with acute myocardial infarction who must receive immediate treatment to relieve the arterial occlusion by, e.g., balloon angioplasty, or otherwise remove the thrombus, may be treated with an intravenous infusion of the α-linolenic acid and/or ETYA preparation prior to and during surgery.

By "α-linolenic acid preparation", "ETYA preparation", and "α-linolenic acid-ETYA preparation" is meant a preparation composed of α-linolenic acid (9,12,15-octadecatrienoic acid), ETYA (5,8,11,14-eicosatetraynoic acid), or a mixture of both α-linolenic acid and ETYA, respectively. This preparation may be either an emulsion of α-linolenic acid and/or ETYA or a composition which contains α-linolenic acid and/or ETYA in addition to a physiologically acceptable carrier, such as human serum albumin. These compositions are suitable for intravenous or intracardial injection into a patient.

By "injection" is meant administration of a solution, normally with a syringe and needle, directly into a selected site where the total volume of the solution is administered over a relatively short period of time (e.g. less than 5 to 10 minutes).

By "intracardial injection" is meant injection of a solution directly into the heart or an artery of the heart.

By "intravenous infusion" is meant gradual introduction of a solution directly into a vein, usually the cephalic or median basilic vein of the arm over an extended period of time (e.g. 30 minutes to several hours or days).

By "ventricular tachyarrhythmia" or "malignant ventricular tachyarrhythmia" is meant an abnormally rapid ventricular rhythm with aberrant ventricular excitation, usually in excess of 150 per minute, which is generated within the ventricle and is most commonly associated with atrioventricular dissociation. Minor irregularities of heart rate may also occur. The rapid beating associated with ventricular tachyarrhythmia renders the heart ineffectual as a pump.

By "ventricular fibrillation" is meant a type of ventricular tachyarrhythmia characterized by rapid, tremulous and ineffectual contractions of the ventricles. Ventricular fibrillation may result from mechanical injury to the heart, occlusion of coronary vessels, effects of certain drugs (such as excess of digitalis, cocaine or chloroform), anaphylactic reactions, electrical stimuli, or ionic imbalance (e.g. calcium, potassium, or sodium).

Ventricular fibrillation may be described as two types. Primary ventricular fibrillation occurs suddenly and unexpectedly in patients with otherwise stable cardiac function. This type of fibrillation is common in the early phase of acute myocardial infarction. Resuscitation of such individuals is highly successful if treated promptly. Secondary ventricular fibrillation occurs as the terminal event in a severely failing heart. At present, resuscitation of patients with secondary ventricular fibrillation is seldom successful.

By "imminent" ventricular tachyarrhythmia or "imminent" ventricular fibrillation is meant an emergency situation in which the patient may proceed from a medical condition involving the heart (e.g., intermittent tachyarrhythmia or heart attack symptoms) to subsequent ventricular fibrillation and cardiac arrest at any moment. Situations involving "imminent" ventricular fibrillation are generally those associated with an emergency room situation (i.e. the patient is at extremely high risk of onset of ventricular fibrillation within hours to minutes). Patients susceptible to "imminent" tachyarrhythmia include those individuals who have developed myocardial ischemia, but may not present with clinical symptoms associated with susceptibility to a heart attack.

By "termination" of ventricular tachyarrhythmia or ventricular fibrillation is meant cessation of arrhythmia associated with ventricular tachyarrhythmia or ventricular fibrillation, and restoration of normal or near normal heart function, such that the patient is no longer at high to extremely high risk of cardiac arrest.

By "ischemia" is meant local and temporary reduction of blood flow due to obstruction of the circulation. By "myocardial ischemic event" is meant an event associated with local and temporary reduction of blood flow due to obstruction of the circulation to the heart. Examples of events associated with induction of myocardial ischemia anaphylactic shock, myocardial infarction, and myocardial disease.

By "ischemia-induced ventricular tachyarrhythmia" or "ischemia-induced ventricular fibrillation" is meant ventricular tachyarrhythmia or ventricular fibrillation which results due to local and temporary obstruction of circulation to the heart.

By "myocardial infarction" is meant the blockage of blood flow to the heart muscle or some portion of the heart muscle that results from a relative or absolute insufficiency of blood supply.

By "patient susceptible to ventricular tachyarrhythmia" and "patient susceptible to ventricular fibrillation" is meant an individual who presents with the conditions described above which may lead to myocardial ischemia.

DETAILED DESCRIPTION

Effects of α-Linolenic Acid and ETYA on Contraction Rate of Myocytes

The ability of α-linolenic acid and ETYA to affect the spontaneous contraction rate of cardiac myocytes was examined in vitro. Cardiac myocytes were isolated from 1 day old rats using the Neonatal Cardiomyocyte Isolation System (Worthington Biochemical Corp., New Jersey) according to the manufacturer's recommendations. This system, utilizing purified enzyme preparations, provides a reliable and consistent cell isolation method. The cells were placed on glass coverslips and cultured at 37° C. in a tissue culture incubator having a 5% $CO_2$ atmosphere with 98% relative humidity. The culture medium was changed every other day. After 48 hours in culture, the cells exhibited regular, spontaneous contractions. The cells were used in experiments after 3–5 days of culture.

During the contractility experiments, a glass coverslip with the attached cultured myocytes was continuously superfused with a HEPES/saline solution (140 mM NaCl, 5 mM KCl, 1.0 mM $MgCl_2$, 1.2 mM $CaCl_2$, 1.0 mM $Na_2HPO_4$, 5.0 mM HEPES, 10 mM glucose, with the pH was adjusted to 7.4 with NaOH). The flow rate was 20 ml/hr. The chamber temperature was maintained at 32° C. The beating rate and amplitude of the contractions of the cultured cardiomyocytes were monitored using a phase contrast microscope and video-monitor edge-detector as described (Crescent Electronics, Salt Lake City). After approximately a 10 min. equilibration period, fatty acid was added to a final concentration of 5–10 μM to the perfusion fluid. Changes in amplitude and rate of cell contractions were used to assess the effects of various fatty acids on cell contractions.

Myocytes were perfused with 5 μM EPA, DHA, AA, or ETYA, or 10 μM of either linoleic acid (C18:2 ω-6), linolenic acid (C18:3 ω-3), oleic acid (C18:1 ω-9), stearic acid (C18:0), myristic acid (C14:0) or lauric acid (C12:0). As summarized in Table I, perfusion of the myocytes with ETYA always reduced the myocyte beating rate within 2 to 3 minutes after addition.

The polyunsaturated fatty acids linoleic acid (C18:2 ω-6) and linolenic acid (C18:3 ω-3) exhibited inhibitory effects on the beating rate similar to ETYA (Table I). The effects of linoleic acid and linolenic acid were less potent (reduction in beating rate by 30–50% within 7 min) when compared with DHA or EPA, which are known to affect myocyte contractility (Billman, et al. 1994 Proc. Natl. Acad. Sci. USA 91:4427–4430). The effects of linoleic and linolenic acid were reversed by perfusion with 0.2% bovine serum albumin (BSA). In contrast, neither mono-saturated fatty acid oleic acid (C18:1 ω-9) nor the saturated fatty acids stearic acid (C18:0), myristic acid (C14:0) and lauric acid (C12:0) affected the contraction rate. Furthermore, EPA-ethyl ester, a non-free acid form of EPA, also did not affect myocyte contractions indicating that the free fatty acid is essential for this effect.

Both ETYA and α-linolenic acid are also effective in terminating contractions induced in cardiac myocytes by arrhythmogenic agents. Both ETYA and linolenic acid were effective in reducing myocyte contractility induced by perfusion of the myocytes with isoproterenol (IPO; 1–5 μM), a known arrhythmogenic agent. Moreover, the myocyte contractions induced by the arrhythmogenic agents lysophosphatidylcholine, acylcarnitine, and ouabain, as well as contractions induced by high extracellular calcium, were terminated by perfusion of the myocytes with α-linolenic acid. These anti-arrhythmogenic effects of ETYA and α-linolenic acid were reversed upon perfusion of the cells with BSA.

To assess whether the effects of polyunsaturated fatty acids on myocyte contraction are due to a change in cardiac myocyte membrane disorder, phytanic acid and cholesterol were used to perfuse the myocytes. Phytanic acid and cholesterol are know to increase and decrease membrane disorder, respectively (Steinberg 1989 "The Metabolic Basis of Inherited Disease", (6th ed.), eds. Scriver et al., McGraw-Hill, New York, pg. 1533–1550). In 7 of 10 measurements, neither phytanic acid (10 μM) nor cholesterol (10 μM) effectively reduced the myocyte beating rate (Table I).

TABLE I

| FATTY ACIDS | NO. CELLS AFFECTED/ NO. CELLS TESTED |
|---|---|
| EPA (20:5 ω-3) | 46/46 (−) |
| DHA (22:6 ω-3) | 32/32 (−) |
| AA (20:4 ω-6) | 18/48 (−), 16/48 (+), 14/48 (±) |
| ETYA (AA analog) | 18/18 (−) |
| AA & Inhibitors | 28/30 (−) |
| linolenic acid (C18:3 ω-3) | 5/5 (−) |

TABLE I-continued

| FATTY ACIDS | NO. CELLS AFFECTED/ NO. CELLS TESTED |
|---|---|
| linoleic acid (C18:2n ω-6) | 4/4 (−) |
| oleic acid (C18:1n ω-9) | 4/4 (±) |
| stearic acid (C18:0) | 6/6 (±) |
| myristic acid (C14:0) | 3/3 (±) |
| lauric acid (C12:0) | 3/3 (±) |
| EPA-ethyl ester | 3/3 (±) |
| Phytanic acid | 9/12 (±), 3/12 (−) |
| Cholesterol | 5/5 (±) |

(−) Inhibitory effect (reduction in beating rate)
(+) Stimulatory effect (increase in beating rate)
(±) No effect (no change in beating rate)

The finding that the effects of the fatty acids on the beating rate took place within 2–5 minutes and addition of fatty acid-free bovine serum albumin promptly reversed the effects of the added fatty acids on the contraction rates, suggests that incorporation of the fatty acids into the membrane phospholipid or other covalent linking to membrane components is not required for their action and that the free fatty acid is the form responsible for the slowing of the beating rate of the myocytes.

Preparation/Isolation of α-Linolenic Acid and ETYA

α-linolenic acid or ETYA, as well as ethyl esters and methyl esters of α-linolenic acid or ETYA, may be obtained from commercial sources (e.g., Sigma). α-linolenic acid may be isolated from vegetable oil employing methods known in the art. Alternative methods of preparation (e.g. chemical synthesis) are known in the art.

Other fatty acids of interest include those fatty acids having ion channel modulating activity. Fatty acids which may exhibit such ion channel modulating activity include omega-3 fatty acids, omega-6 fatty acids, and derivatives of omega-3 or omega-6 fatty acids. Methods for the identification, isolation and screening of these fatty acids is known in the art (Hallaq et al. 1992 *Proc. Natl. Acad. Sci. USA* 89:1760–1764).

Preparation of α-linolenic acid or ETYA for administration

α-linolenic acid and/or ETYA may be administered as a suspension in a physiologically acceptable carrier suitable for intravenous injection into a patient, e.g. albumin, sterile saline. Preferably, the physiological acceptable carrier for α-linolenic acid and/or ETYA is fatty acid-free albumin, more preferably fatty acid-free human serum albumin. Administration of α-linolenic acid and/or ETYA with fatty acid-free albumin can serve to reduce the effective dose of the fatty acid necessary to prevent or terminate ventricular tachyarrhythmia or ventricular fibrillation by as much as one-tenth of the dose required in the absence of the albumin carrier. The amount of albumin present in the composition for injection may vary considerably, but generally the concentration of the albumin will be such that the albumin and total concentration of α-linolenic acid and/or ETYA are present in a ratio of 1 molecule albumin to 6 molecules of fatty acid. Delipidated (fatty acid-free) human serum albumin is commercially available, or may be obtained by methods well-known in the art.

Salts (e.g. sodium salts) of α-linolenic acid and/or ETYA rather than the free fatty acid, may be employed. To facilitate suspension of the α-linolenic acid and/or ETYA composition, (i.e. formation of a preparation), a suitable emulsifying agent (e.g., lecithin) may be used. The α-linolenic acid and/or ETYA preparation may further include additional agents such as anti-thrombotic agents, blood thinning agents, pain-relieving agents, and nutrients such as glucose.

Identification of Patients

The therapy of the invention can be employed for acute treatment of a patient presenting with a myocardial infarction or other condition which renders the patient susceptible to imminent ventricular tachyarrhythmia, or imminent ventricular fibrillation which may result in sudden death. The therapy of the invention can also be employed to treat (i.e. terminate) ventricular fibrillation, or other ventricular arrhythmias, after onset of in the susceptible patients.

Myocardial infarction is an example of a myocardial disease associated with myocardial ischemia, and thus risk of ventricular tachyarrhythmia and imminent ventricular fibrillation. Myocardial infarction is usually associated with a classic clinical syndrome with sudden onset of characteristic symptoms, followed by serial electrocardiographic changes and transient rises in the serum levels of enzymes released from the myocardium. In the classic syndrome, a sudden, total occlusion of a major coronary artery by thrombosis causes infarction involving a left ventricular wall in the specific region supplied by the affected artery. In these cases, the artery may be totally occluded within six hours after the onset of symptoms. In other instances the occlusion of the artery is less sudden or less complete and the resulting infarction occurs during a period of hours or days and may be less localized. It should be noted that other, non-occlusive ischemic episodes may produce the same effects as occlusive myocardial disease.

Myocardial infarction may result in deaths that occur instantaneously or within minutes after the onset of ischemic symptoms. Myocardial infarction may arise from a sudden severe disparity between myocardial oxygen supply and demand in the absence of acute changes in the caliber of the coronary arteries; for example, a sudden reduction in oxygen supply caused by a drop in blood pressure during anesthesia and surgery may precipitate myocardial infarction. An acute increase in oxygen demand resulting from such stresses as heavy exertion, acute hypertension, an excess of catecholamines or cocaine abuse may also precipitate myocardial infarction. Myocardial fibrosis, which results from ischemia to heart muscle, may also predispose an individual to ventricular tachyarrhythmia and/or ventricular fibrillation when subjected to a further acute ischemic event. The initial myocardial fibrosis may develop during a period of months or years in patients with coronary artery disease who do not present with acute clinical episodes.

In patients presenting with classical acute myocardial infarction, the first symptom is usually chest pain, typically similar to angina pectoris but more severe, more persistent, and unrelieved by nitroglycerin. Radiation of the pain or its localization to the neck, jaw, shoulder or left arm occurs as in angina; pain in the epigastrium, simulating that of indigestion, is particularly frequent. Marked sweating, almost from the onset of pain, is characteristic, and nausea and vomiting are common.

Physical examination typically reveals a patient with continuing chest pain who prefers to lie quietly in the supine position and is in evident acute distress. The skin is usually cool, moist and pale. The pulse may be rapid or slow and the blood pressure may be elevated or reduced. Heart sounds are often faint and an $S_4$ (atrial gallop) is often present. An $S_3$ (ventricular gallop), inspiratory rales and elevated jugular venous pressure are signs of congestive heart failure and are observed in only a minority of patients at the initial presentation. Pericardial friction rubs are rarely heard initially. Electrocardiogram (ECG) examination reveals the development of pathological Q waves and serial ST segment and T wave changes. These patterns are virtually diagnostic in themselves. Some patients may present with only changes in the ST segments and T waves. Two-dimensional echocardiography demonstrates abnormalities that occur in acute myocardial infarction as early as the within the first few minutes or hours after onset. This procedure is useful in the initial evaluation of the patient, particularly when the ECG is not diagnostic or the diagnosis is in doubt. The extent of the wall motion abnormality is helpful in assessment of the initial prognosis and likelihood of complications. Abnormal bulging of the atrial septum toward the left atrium in patients with acute inferior myocardial infarction is an indicator of right ventricular infarction.

Not all patients with acute myocardial infarction, and/or myocardial ischemia, present with classical symptoms. For example, diabetic patients may be especially likely to have acute myocardial infarction without experiencing chest pain because of neuropathy involving the neural pathways in the thorax that carry visceral pain signals. (Airaksinen et al. 1992 association between silent coronary artery disease, diabetes and autonomic neuropathy: fact or fallacy? *Diabetes Care* 15:288). Onset of myocardial infarction in elderly patients presents most frequently presents with sudden dyspnea or exacerbation of chronic congestive heart failure. Acute confusion, dizziness, syncope, stroke or new arrhythmia may also be the presenting symptom. (Aronow 1987 Prevalence of presenting symptoms of recognized acute myocardial infarction and of unrecognized healed myocardial infarction in elderly patients. *Am J Cardiol* 60:1182) Postoperative infarction may be difficult to recognize by classical symptoms due to concurrent medical circumstances (e.g. pain, use of analgesic drugs).

Laboratory diagnosis during acute phase reveals a rise in serum levels of creatine kinase or its MB isoenzyme, which is detectable within 3 hours after pain onset in typical cases of acute myocardial infarction. Levels of lactate dehydrogenase (LDH) are also indicative of the onset of acute myocardial infarction; LDH levels remain elevated for up to a week or longer after onset. Radionuclide imaging or magnetic resonance imaging may also be employed in diagnosis of infarction.

Patients who have had a previous infarction experience a recurrence of myocardial infarction after noncardiac surgery, particularly after thoracic or abdominal surgery or when surgery is performed within 6 months after an infarction. (Steen et al. 1978 Myocardial reinfarction after anesthesia and surgery *JAMA* 239:2566) Incidence of mortality in such cases is high.

The therapy of the invention can also be employed for treatment of patients who may have a potentially lethal arrhythmia. Patients with a potentially lethal arrhythmia are identified by, for example, electrocardiogram, echocardiography, or other methods of analysis of cardiac function described above. Patients with potentially lethal arrhythmias may be either symptomatic (e.g. have intermittent chest pain) or asymptomatic. Examples of potentially lethal arrhythmias include arrhythmias which result from a birth defect.

Identification of arrhythmias and testing of the efficacy of a therapy selected for controlling an identified arrhythmia involves an invasive procedure. A catheter containing an electrode is placed into the patient's heart. The cardiac electrophysiologist then applies a programmed electrical stimulation of the heart muscle to elicit the suspected arrhythmia. Once the arrhythmia is induced, the heart is defibrillated. The clinician then chooses a medication for the patient. After the patient has received this therapy for about 6 to 8 weeks, the clinician again performs the invasive electrostimulation test described above, and attempts to induce the previously observed arrhythmia. If the arrhythmia is not elicited by electrostimulation, the therapy is continued. If the electrostimulation successfully elicits the arrhythmia, the clinician prescribes an alternate therapy and the patient returns to the hospital 6 to 8 weeks later to repeat the electrostimulation procedure. Alternatively, the patient is admitted to the hospital for implantation of an electronic defibrillator.

The composition of α-linolenic acid and/or ETYA of the invention can shorten this potentially lengthy, invasive procedure since these compounds are effective within seconds to minutes after administration. After the arrhythmia is induced by electrostimulation and the patient's heart is defibrillated, the composition of the invention composed of α-linolenic acid and/or ETYA is administered either by intravenous infusion or direct intracardial injection. Because these compounds are effective within seconds to minutes after administration, the clinician can then immediately repeat the electrostimulation test to determine whether these compounds are effective in preventing the arrhythmia. Therefore, only one catherization in the electrostimulation testing procedure may be necessary, thus reducing the need for repeated, invasive procedures.

Timing of Administration

The α-linolenic acid and/or ETYA preparation may be administered to the patient immediately upon presentation of symptoms associated with risk of imminent ventricular tachyarrhythmia and/or ventricular fibrillation, such as those associated with myocardial ischemia or acute myocardial infarction, or immediately upon or after onset of ventricular tachyarrhythmia, particularly ventricular fibrillation. Where the patient is susceptible to ventricular tachyarrhythmia, the composition of the subject invention may be administered immediately upon identification of the tachyarrhythmia in the patient. Where the patient is susceptible to imminent ventricular fibrillation, the composition of the subject invention is preferably administered within 24 hours, more preferably within 3 hours of onset of myocardial ischemia. Treatment may be continued until the arterial occlusion is relieved (e.g. balloon angioplasty) and/or the patient is in stable or non-critical condition. In general, treatment may be continued for up to one week, usually no longer than 4 days, more usually no longer than 48 hours.

Mode Of Administration

Where the patient presents with symptoms which constitute an emergency situation (e.g. symptoms of heart attack and imminent ventricular fibrillation or existing ventricular fibrillation), the patient may receive an initial bolus of the α-linolenic acid and/or ETYA preparation by direct injection into the heart or an artery of the heart. As an alternative or supplement to the direct intracardial injection, the patient may receive the α-linolenic acid and/or ETYA preparation as an intravenous infusion. The α-linolenic acid and/or ETYA preparation may be administered from a container adapted for the desired mode of administration, such as an I.V. bottle for intravenous infusion or from a syringe and needle for direct intracardial injection.

Dosages of the α-linolenic acid and/or ETYA preparation appropriate for human use can be extrapolated from dosages appropriate for non-human animal use depending on the weight of the animal. For example, it is expected that the concentrations of α-linolenic acid and/or ETYA and the rate of delivery found to be appropriate for dogs will be comparable to the parameters appropriate for human administration. Determination of effective dosages for humans is thus routine to one of ordinary skill in the art and will vary according to many factors including patient age, size (e.g. weight), and arrhythmic state (i.e. time of administration relative to onset of ventricular fibrillation; level of risk of patient to ventricular arrhythmia) (see, for example, Remington's Pharmaceutical Sciences (18th edition), 1990, Gennaro, et al. eds.). Where the composition for administration contains albumin in addition to α-linolenic acid and/or ETYA, the effective dosage may be significantly reduced.

While the concentrations of each of α-linolenic acid or ETYA in the preparation may vary, the total concentration of α-linolenic acid and/or ETYA should be less than 10 to 30% by volume of the preparation where α-linolenic acid and/or ETYA are not conjugated to a carrier and the preparation is administered at normal intravenous infusion rates which are well known in the art. Appropriate, physiologically acceptable carriers for use in the α-linolenic acid and/or ETYA preparation are known in the art. Preparations with concentrations greater than 10 to 30% by volume α-linolenic acid and/or ETYA are not desirable for direct intravenous infusion due to the toxicity associated with administration of high concentrations of α-linolenic acid and/or ETYA.

Encapsulation of α-linolenic acid and/or ETYA in lipid vesicle carriers can allow for non-toxic administration of preparations comprising greater than 10 to 30% by volume α-linolenic acid and/or ETYA. Lipid vesicles made of, for example, egg lecithin may allow for slow release of the α-linolenic acid and/or ETYA. Alternatively, although less desirably, the toxicity of administration of preparations comprising total concentrations of α-linolenic acid and/or ETYA greater than 10 to 30% by volume may be avoided by reducing the rate of intravenous infusion.

The preparation may be composed of α-linolenic acid, ETYA, or a mixture of α-linolenic acid and ETYA at an appropriate effective, non-toxic concentration, usually at least 5% to 10% by volume, preferably at least 0.002% to 5%, more preferably at least 0.002%, even more preferably at least 0.001% to 0.002%, with a final total dosage of 3.5 g to 10 g α-linolenic acid and/or ETYA being administered to the patient. A final total dosage of 2 g of α-linolenic acid and/or ETYA or less may be effective. The total amount of α-linolenic acid and/or ETYA may be administered as an intravenous infusion at a rates ranging from approximately $5 \times 10^{-7}$ to $2 \times 10^{-5}$ mole/kg/min.

What is claimed is:

1. A method for preventing imminent ventricular tachyarrhythmia, said method comprising the steps of:

identifying a patient at risk of imminent ventricular tachyarrhythmia; and infusing intravenously into said patient a composition comprising more than zero and less than or equal to 30% by volume of eicosatetraynoic acid in an amount being sufficient to prevent imminent ventricular tachyarrhythmia.

2. The method of claim 1, wherein said ventricular tachyarrhythmia is ventricular fibrillation.

3. The method of claim 1, wherein said patient has had a myocardial ischemic event and said infusing is carried out within 24 hours of onset of the myocardial ischemic event in said patient.

4. The method of claim 1, wherein said composition comprises at least 0.002% by volume eicosatetraynoic acid.

5. The method of claim 1, further comprising, prior to the step of infusing said composition, the step of injecting said composition intracardially into said patient.

6. The method of claim 5, wherein said ventricular tachyarrhythmia is ventricular fibrillation, said patient has had a myocardial ischemic event, and said infusing is carried out within 24 hours of the onset of the myocardial ischemic event in said patient.

7. The method of claim 6, wherein said composition comprises at least 0.002% by volume eicosatetraynoic acid.

8. A method for preventing imminent ventricular tachyarrhythmia, said method comprising the steps of:

identifying a patient at risk of imminent ventricular tachyarrhythmia; and injecting intracardially into said patient a composition comprising more than zero and less than or equal to 30% by volume of eicosatetraynoic acid in an amount being sufficient to prevent imminent ventricular tachyarrhythmia.

9. The method of claim 8, wherein said ventricular tachyarrhythmia is ventricular fibrillation.

10. The method of claim 8, wherein said patient has had a myocardial ischemic event, and said infusing is carried out within 24 hours of onset of the myocardial ischemic event in said patient.

11. The method of claim 10, wherein said composition comprises at least 0.002% by volume eicosatetraynoic acid.

12. A method for terminating ventricular tachyarrhythmia, said method comprising the steps of:

identifying a patient having a ventricular tachyarrhythmia; and infusing intravenously into said patient a composition comprising more than zero and less than or equal to 30% by volume of eicosatetraynoic acid in an amount being sufficient to terminate said ventricular tachyarrhythmia.

13. The method of claim 15, wherein said ventricular tachyarrhythmia is ventricular fibrillation.

14. The method of claim 15, wherein said patient has had a myocardial ischemic event, and said infusing is carried out within 24 hours of onset of the myocardial ischemic event in said patient.

15. The method of claim 12, wherein said composition comprises at least 0.002% by volume eicosatetraynoic acid.

16. The method of claim 12, further comprising, prior to the step of infusing said composition, the step of injecting said composition intracardially into said patient.

17. The method of claim 16, wherein said ventricular tachyarrhythmia is ventricular fibrillation, said patient has had a myocardial ischemic event and said injecting is carried out within 24 hours of onset of the myocardial ischemic event in said patient.

18. The method of claim 16, wherein said composition comprises at least 0.002% by volume eicosatetraynoic acid.

19. A method for terminating ventricular tachyarrhythmia, said method comprising the steps of:

identifying a patient having ventricular tachyarrhythmia; and injecting intracardially into said patient a composition comprising more than zero and less than or equal to 30% by volume of eicosatetraynoic acid in an amount being sufficient to terminate said ventricular tachyarrhythmia.

20. The method of claim 19, wherein said ventricular tachyarrhythmia is ventricular fibrillation.

21. The method of claim 19, wherein said patient has had a myocardial ischemic event, and said injecting is carried out within 24 hours of onset of the myocardial ischemic event in said patient.

22. The method of claim 19, wherein said composition comprises at least 0.002% by volume eicosatetraynoic acid.

* * * * *

UNITED STATES PATENT AND TRADEMARK OFFICE
CERTIFICATE OF CORRECTION

PATENT NO. : 5,541,225

DATED : July 30, 1996

INVENTOR(S) : Alexander Leaf and Jing X. Kang

It is certified that error appears in the above-identified patent and that said Letters Patent is hereby corrected as shown below:

Title page, item [56], under "References Cited", add the following:

| | | |
|---|---|---|
| 4,607,052 | 08/19/86 | Mendy et al. |
| 4,678,808 | 07/07/87 | Ward et al. |
| 5,089,268 | 02/18/92 | Katz |
| 2-1369520 | 1/31/92 | Japan |
| 04244023-A | 09/01/92 | Japan |

Steen et al., "Myocardial Reinfarction After Anesthesia and Surgery," *JAMA* (Jun 1978) 239(24):2566-2570.

McLennan et al., "Influence of Dietary Lipids on Arrhythmias and Infarction After Coronary Artery Ligation in Rats," *Can. J. Physiol. Pharmacol.* (Nov 1985) 63:1411-1417.

Aronow, "Prevalence of Presenting Symptoms of Recognized Acute Myocardial Infarction and of Unrecognized Healed Myocardial Infarction in Elderly Patients," *Am. J. Cardiol.* (Nov 1987) 60:1182.

Juan et al., "Effect of exogenous 5, 8, 11, 14, 17-eicosapentaenoic acid on cardiac anaphylaxis," *Br. J. Pharmacol.* (Feb 1987) 90:315-325.

Leaf et al., "Cardiovascular Effects of n-3 Fatty Acids," *New England Journal of Medicine* (Mar 1988) 318:549-

UNITED STATES PATENT AND TRADEMARK OFFICE
CERTIFICATE OF CORRECTION

PATENT NO.   : 5,541,225

DATED        : July 30, 1996

INVENTOR(S)  : Alexander Leaf and Jing X. Kang

It is certified that error appears in the above-identified patent and that said Letters Patent is hereby corrected as shown below:

McLennan et al., "Dietary Fish Oil Prevents Ventricular Fibrillation Following Coronary Artery Occlusion and Reperfusion," *Am Heart J* (Sep 1988) 116:709-717.

Billman, "Effect of Calcium Channel Antagonists on Susceptibility to Sudden Cardiac Death: Protection from Ventricular Fibrillation," *J. Pharmacol. Exp. Therap.* (Mar 1989) 248:1334-1342.

Leaf, "Cardiovascular Effects of Fish Oils: Beyond the Platelet," *Circulation* (Aug 1990) 82:624-628.

Hallaq et al., "Protective effect of eicosapentaenoic acid on ouabain toxicity in neonatal rat cardiac myocytes," *Proc. Natl. Acad. Sci. USA* (Oct 1990) 87:7834-7838.

Makita et al., "Successful Management of Life-Threatening Ventricular Arrhythmias with Propafenone in a Hemodialysis Patient," *Curr. Ther. Res.* (Jun 1991) 49:954-960.

Yamashita et al., "Effect of Eicosapentaenoic and Docosahexaenoic Acid on Natural Killer Cell Activity in Human Peripheral Blood Lymphocytes," *Clin. Immunol. Immunopathol.* (Jun 1991) 59:335-345.

UNITED STATES PATENT AND TRADEMARK OFFICE
CERTIFICATE OF CORRECTION

PATENT NO. : 5,541,225

DATED : July 30, 1996

INVENTOR(S) : Alexander Leaf and Jing X. Kang

It is certified that error appears in the above-identified patent and that said Letters Patent is hereby corrected as shown below:

Yamazaki et al., "Changes in fatty acid composition in rat blood and organs after infusion of docosahexaenoic acid ethyl ester," *Am. J. Clin. Nutr.* (Mar 1991) 53:620-627.

Billman et al., "Elevated Myocardial Calcium and its Role in Sudden Cardiac Death," *FASEB J* (Aug 1991) 5:2586-2592.

Hallaq et al., "Modulation of Dihydropyridine-sensitive Calcium Channels in Heart Cells by Fish Oil Fatty Cells," *Proc. Natl. Acad. Sci. USA* (Mar 1992) 89(5):1760-1764.

Billman, Ro 40-5967, a Novel Calcium Channel Antagonist, Protects Against Ventricular Fibrillation," *Eur. J. Pharmacol.* (Dec 1992) 229:179-187.

Billman, "The Calcium Channel Antagonist, Flunarizine, Protects Against Ventricular Fibrillation," *Eur. J. Pharmacol.* (Mar 1992) 212:231-235.

Airaksinen et al., "Association Between Silent Coronary Artery Disease, Diabetes, and Autonomic Neuropathy. Fact or Fallacy?" *Diabetes Care* (Feb 1992) 15:288-292.

Billman, "Effect of Calcium Channel Antagonists on Cocaine-Induced Malignant Arrhythmias: Protection Against Ventricular Fibrillation," *J. Pharmacol. Exp. Ther.* (Jul 1993) 266:407-416.

UNITED STATES PATENT AND TRADEMARK OFFICE
CERTIFICATE OF CORRECTION

PATENT NO. : 5,541,225

DATED : July 30, 1996

INVENTOR(S) : Alexander Leaf and Jing X. Kang

It is certified that error appears in the above-identified patent and that said Letters Patent is hereby corrected as shown below:

Steinberg, 1989, "Refsum Disease," Chapter 59, In: "The Metabolic Basis of Inherited Disease," 6th ed., Scriver et al., McGraw-Hill, New York, pgs. 1533-1550.

Billman, "Prevention of ischemia-induced ventricular fibrillation by ω3 fatty acids," *Proc. Natl. Acad. Sci. USA*, (May 1994) 91:4427-4430.

Title page, column 2, under

"PUBLICATIONS", "Murnaghan", "Effect of Fatty Acids...", replace "Heast" with --Heart--;

Column 4, line 50, replace "know" with --known--;

Column 7, line 5, after "early as", delete --the--.

Signed and Sealed this

Seventeenth Day of December, 1996

*Attest:*

*Attesting Officer*

BRUCE LEHMAN

*Commissioner of Patents and Trademarks*